(12) United States Patent
Lees et al.

(10) Patent No.: US 6,284,250 B1
(45) Date of Patent: Sep. 4, 2001

(54) SIMPLIFIED METHOD FOR REMOVING FREE PROTEIN DURING PREPARATION OF PROTEIN-POLYSACCHARIDE CONJUGATES AND VACCINES USING RESTRICTED-ACCESS MEDIA

(75) Inventors: Andrew Lees, Silver Spring; Douglas E. Shafer, Gambrills, both of MD (US)

(73) Assignee: The Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 09/244,178

(22) Filed: Feb. 4, 1999

Related U.S. Application Data

(60) Provisional application No. 60/073,790, filed on Feb. 5, 1998.

(51) Int. Cl.⁷ .................. A61K 39/00; A61K 39/385; C07K 1/16; C07K 1/22; C07K 1/34

(52) U.S. Cl. .................. 424/193.1; 424/196.11; 424/197.11; 530/403; 530/415; 530/416; 530/417; 536/127

(58) Field of Search ............ 424/193.1, 196.11, 424/197.11; 530/403, 415, 416, 417; 536/127

(56) References Cited

U.S. PATENT DOCUMENTS

| | | | |
|---|---|---|---|
| 4,057,685 | 11/1977 | McIntire | 536/18 |
| 4,923,978 | 5/1990 | McCormick | 536/27 |
| 4,929,560 | 5/1990 | Edmunds et al. | 435/226 |
| 5,106,966 | 4/1992 | Thomas et al. | 536/27 |
| 5,277,813 | 1/1994 | Feibush et al. | 210/502.1 |
| 5,306,492 | 4/1994 | Porro | 424/88 |
| 5,651,971 | * 7/1997 | Lees | 424/194.1 |
| 5,993,825 | * 11/1999 | Jennings et al. | 424/244.1 |
| 6,013,267 | * 1/2000 | Blake et al. | 424/249.1 |

FOREIGN PATENT DOCUMENTS

| | | |
|---|---|---|
| 646 594 A1 | 4/1995 | (EP) . |
| WO 96/29094 | 9/1996 | (WO) . |
| WO 96/40242 | 12/1996 | (WO) . |
| WO 97/20853 | 6/1997 | (WO) . |

OTHER PUBLICATIONS

Notes & Tips, Analytical Biochemistry 250, 257–260 (1997), Article No. AB972248, 0003–2697/97.

Water Oasis™ HLB Extraction Cartridges Applications Notebook First Edition, Aug. 1996.

K.–S. Boos and Anne Rudolphi, The Use of Restricted–Access Media in HPLC, Part I—Classification and Review, Sample Prep Perspectives, LC–GC vol. 15, No. 7, Jul. 1997.

(List continued on next page.)

Primary Examiner—David Saunders
(74) Attorney, Agent, or Firm—Finnegan, Henderson, Farabow, Garrett & Dunner, L.L.P.

(57) ABSTRACT

Removing free protein from a liquid mixture containing the protein and a protein-polysaccharide conjugate can be a technologically difficult, expensive, and time consuming process. The procedure described herein for removing the protein from such a mixture simplifies this removal. The procedure includes contacting the liquid mixture, including the protein and the protein-polysaccharide conjugate, with a solid phase, restricted-access media material. This material at least partially binds with the protein and separates it from the liquid mixture, thereby providing a purified liquid containing at least a portion of the protein-polysaccharide conjugate and a reduced amount of the protein. The purified liquid can be collected for further processing or use. As one example, the restricted-access media material can include porous silica particles that generally allow the protein to enter, but restrict or limit access to the protein-polysaccharide conjugate. In this manner, at least some of the free protein adheres, attaches, or otherwise binds to the restricted-access media material and separates from the conjugate. The process of the invention can be used for preparing protein-polysaccharide conjugates that can be used in vaccines or other pharmaceutical compositions.

14 Claims, 9 Drawing Sheets

OTHER PUBLICATIONS

Anne Rudolphi and K.-S. Boos, The Use of Restricted-Access Media in HPLC, Part II—Applications, Sample Prep Perspectives, LC-GC vol. 15, No. 9, Sep. 1997.

Herraiz, T. et al, "Evaluation of Solid–Phase Extraction Procedures in Peptide Analysis," Journal of Chromatography A, vol. 708, (1995), pp. 209–221.

PCT Search Report, PCT/US99/02416, mailed May 28, 1999.

* cited by examiner

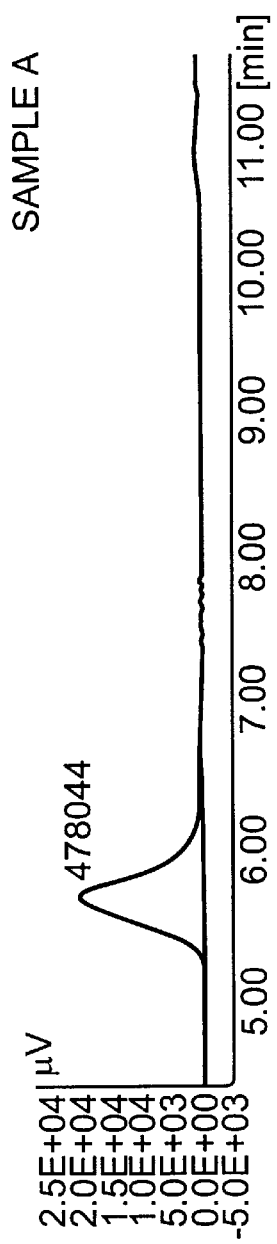
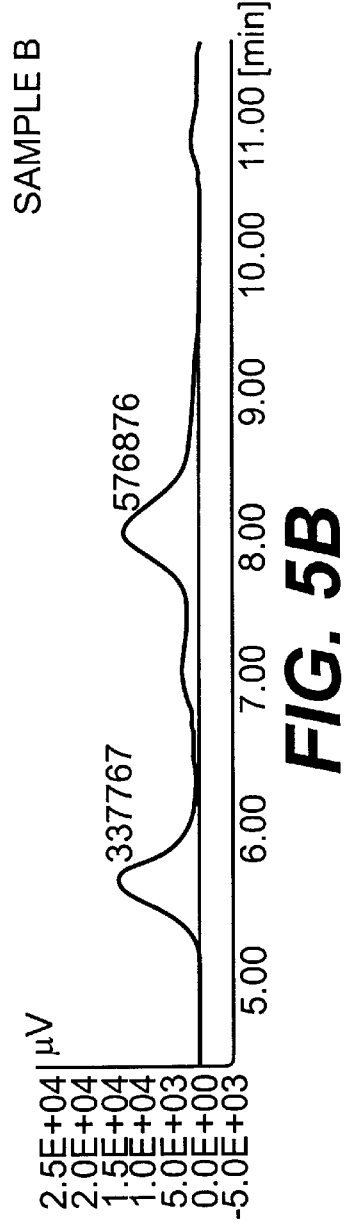
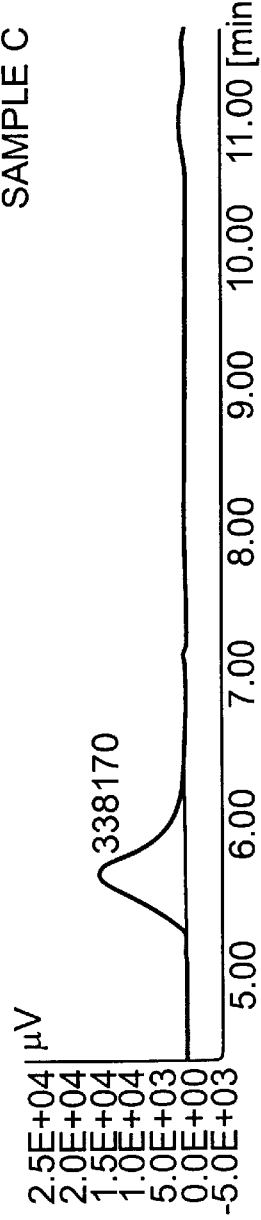
FIG. 5A  SAMPLE A
FIG. 5B  SAMPLE B
FIG. 5C  SAMPLE C

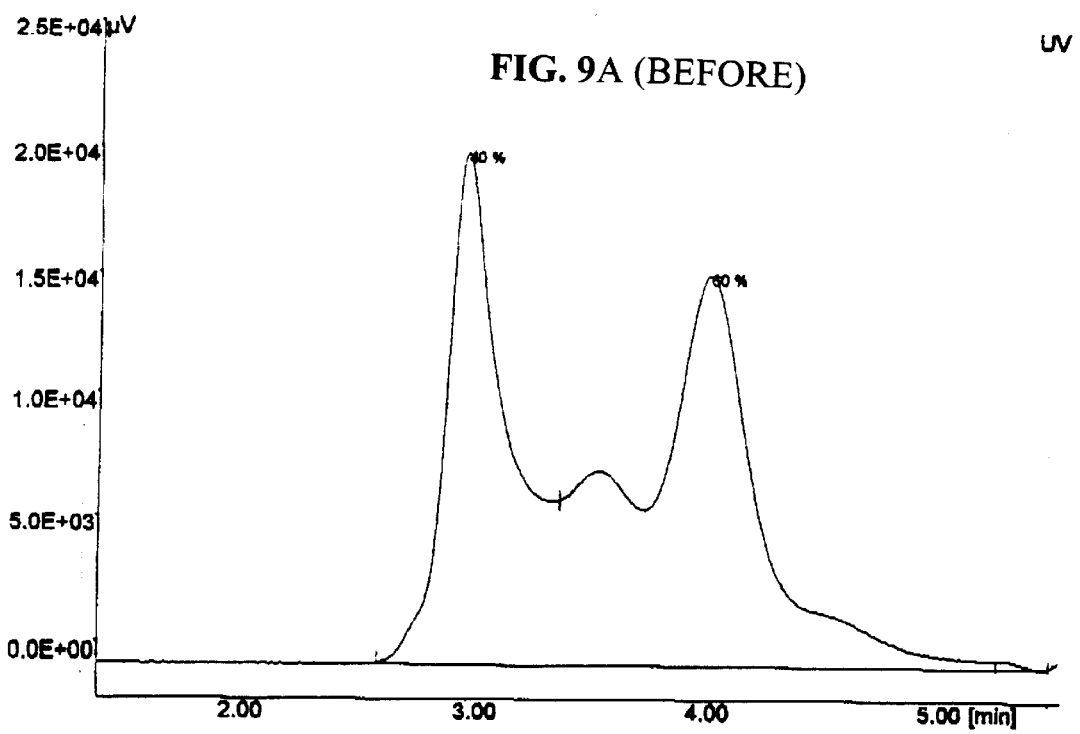
FIG. 9A (BEFORE)
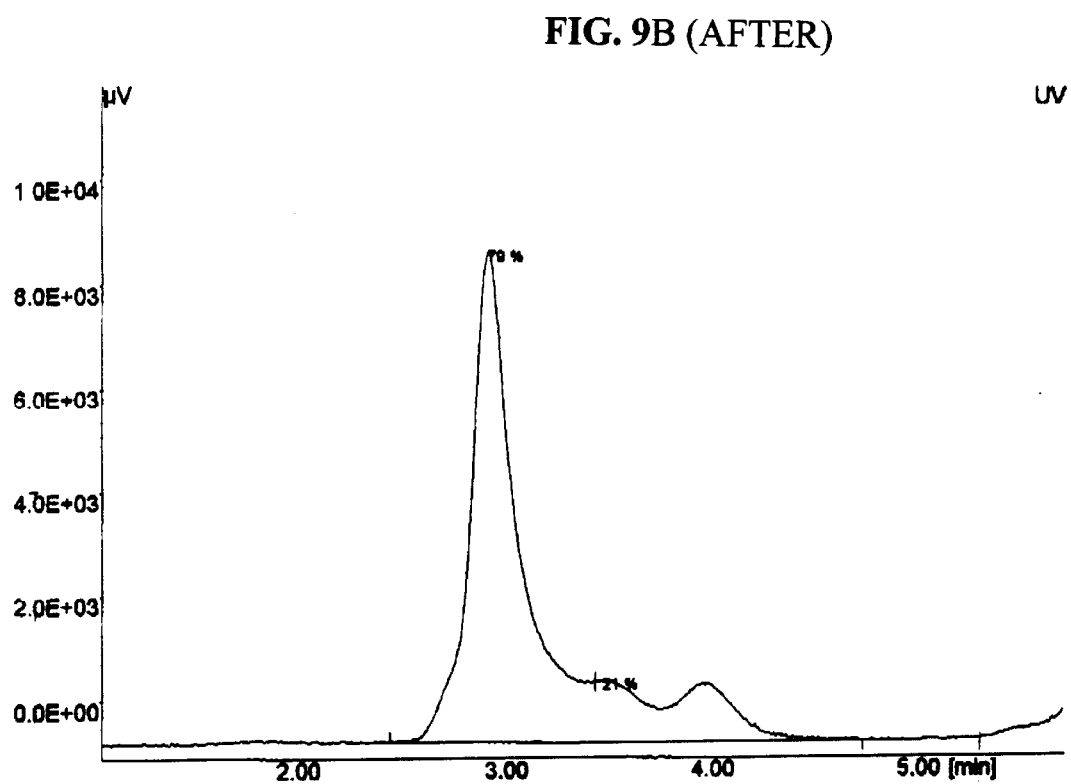
FIG. 9B (AFTER)

SIMPLIFIED METHOD FOR REMOVING FREE PROTEIN DURING PREPARATION OF PROTEIN-POLYSACCHARIDE CONJUGATES AND VACCINES USING RESTRICTED-ACCESS MEDIA

CROSS-REFERENCE TO RELATED APPLICATIONS

This application claims the benefit of U.S. Provisional Application Ser. No. 60/073,790, filed Feb. 5, 1998, which is hereby incorporated by reference.

BACKGROUND OF THE INVENTION

Vaccines have been very effective in protecting people from a wide variety of diseases, whether caused by virus, bacteria, or fungus. The ability of vaccines to induce specific protection against such a wide range of pathogenic organisms results from their ability to stimulate specific humoral antibody responses, as well as cell-mediated responses. This invention relates to a process for preparing such vaccines, and particularly to a process for making protein-polysaccharide conjugates that are used in preparing vaccines, immunogens, and other valuable immunological reagents. The invention further relates to the vaccines and other compositions produced from the conjugates made according to the invention.

Certain agents can stimulate an immune response with minimal chemical modifications, for example, tetanus toxoid, which is immunogenic even in the absence of an adjuvant. Other important agents are either non-immunogenic or poorly immunogenic, but they can be converted into immunogenic molecules or constructs, in which form they can induce vigorous immune responses. For example, most polysaccharides are poorly immunogenic in young animals. After they are coupled to proteins, however, the resulting construct becomes immunogenic. For example, immunization with protein-polysaccharide conjugates enables otherwise unresponsive young children to mount an immune response to the polysaccharide component. The conjugation of proteins to polysaccharides converts the polysaccharide from a weakly immunogenic T-cell independent antigen to a T-cell dependent antigen that recruits T-cell help, and thus stimulates heightened immune responses. Note the discussion by J. M. Cruse, et al. (Editors), *Conjugate Vaccines*, Karger, Basel, (1989); and R. W. Ellis, et al. (Editors), *Development and Clinical Uses of Haemophilus B Conjugate Vaccines*, Marcel Dekker, New York (1994). These books are entirely incorporated herein by reference.

Conjugation of a protein and a polysaccharide can provide other advantageous results. For example, it has been found that protein-polysaccharide conjugates enhance the antibody response not only to the polysaccharide component, but also to the protein component. This effect is described, for example, in the dual conjugate patent applications of Mond and Lees, U.S. patent appln. Ser. No. 08/402,565 (filed Mar. 13, 1995) (now abandoned), now U.S. Pat. No. 5,585,100 (issued Dec. 17, 1996); Appln. Ser. No. 08/444,727 (filed May 19, 1995); and Appln. Ser. No. 08/468,060 (filed Jun. 6, 1995) (now abandoned). These patent applications each are entirely incorporated herein by reference. This effect also is described in A. Lees, et al., "Enhanced Immunogenicity of Protein-Dextran Conjugates: I. Rapid Stimulation of Enhanced Antibody Responses to Poorly Immunogenic Molecules," *Vaccine*, Vol. 12, No. 13, (1994), pp. 1160–1166. This article is entirely incorporated herein by reference.

Noting at least some of the advantageous results obtained using protein-polysaccharide conjugates, researchers have developed various techniques to facilitate coupling of proteins and polysaccharides. Note W. E. Dick, et al., "Glyconjugates of Bacterial Carbohydrate Antigens: A Survey and Consideration of Design and Preparation Factors," *Conjugate Vaccines* (Eds. Cruse, et al.), Karger, Basel, 1989, beginning at page 48. This article also is entirely incorporated herein by reference. As one example of a protein-polysaccharide coupling technique, the use of organic cyanylating reagents, such as 1-cyano-4-(dimethylamino)-pyridinium tetrafluoroborate, also called "CDAP" in this patent application, has been developed. These reagents activate polysaccharides and facilitate coupling of polysaccharides to proteins for conjugate vaccines. The activated polysaccharides can be directly or indirectly coupled to proteins. The use of CDAP and other organic cyanylating reagents is described in the following U.S. Patent and Patent Applications of Andrew Lees: U.S. patent appln. Ser. No. 08/124,491 (filed Sep. 22, 1993, now abandoned); U.S. Pat. No. 5,651,971; U.S. Pat. No. 5,693,326; and U.S. patent appln. Ser. No. 08/482,666 (filed Jun. 7, 1995) (now U.S. Pat. No. 5,849,301). These U.S. patents and patent applications each are entirely incorporated herein by reference. The use of CDAP also is described in Lees, et al., "Activation of Soluble Polysaccharides with 1-Cyano-4-Dimethylamino Pyridinium Tetrafluoroborate For Use in Protein-Polysaccharide Conjugate Vaccines and Immunological Reagents," *Vaccine*, Vol. 14, No. 3 (1996), pp. 190–198. This article also is entirely incorporated herein by reference.

Other techniques for coupling proteins and polysaccharides also are known. For example, the use of homobifunctional or heterobifunctional vinylsulfones for protein-polysaccharide conjugation is described in U.S. patent appln. Ser. No. 08/852,733 filed on May 7, 1997, (pending) in the name of Andrew Lees. Protein-polysaccharide coupling using uronium salts and haloacyl reagents is described in U.S. Provisional Patent Appln. Nos. 60/041,781 (filed Mar. 24, 1997) and 60/042,379 (filed Apr. 24, 1997), respectively. These patent applications also are entirely incorporated herein by reference.

In the production of protein-polysaccharide conjugates and vaccines, a major cost and time consuming step lies in the separation of the free protein (i.e., the unreacted or non-conjugated protein that is not covalently bound to a polysaccharide) from the conjugated protein-polysaccharide product. This separation, which is also called "fractionation," usually is accomplished using a column chromatographic technique (e.g., size exclusion chromatography or gel filtration) or an ultrafiltration process. These protein separation processes significantly increase the time and expense involved in producing protein-polysaccharide conjugates and vaccines. Under the good manufacturing procedure ("GMP") guidelines, a dedicated (and expensive) chromatography column normally is needed for each type of conjugate to prevent contamination of the product.

In addition to the increased production cost and time, this free protein separation step often results in a significant loss of the desired protein-polysaccharide conjugate material because the conjugate does not easily release from the chromatographic matrix. This factor further increases the costs involved in preparing a protein-polysaccharide conjugate vaccine.

Given the state of the art as described above, there is a need for a simple, quick, and efficient procedure for separating free protein from a mixture that contains free protein and a protein-polysaccharide conjugate.

SUMMARY OF THE INVENTION

This invention relates to a process for separating free protein from a mixture including a protein-polysaccharide conjugate and/or a polysaccharide that avoids use of the expensive and time consuming techniques described above (e.g., column chromatography or size exclusion chromatography). Thus, this invention provides a convenient, inexpensive, and effective procedure for removing free protein from a liquid mixture including a protein-polysaccharide conjugate.

In a first aspect, the invention relates to a method for removing free protein from a liquid mixture containing the free protein and at least one member selected from the group consisting of a protein-polysaccharide conjugate and a polysaccharide. The liquid mixture may contain more than one type of free protein, each of which is separated from the conjugate and/or polysaccharide in the process of the invention. This method includes contacting the liquid mixture with a solid phase, restricted-access media material, wherein the solid phase, restricted-access media material at least partially binds with the free protein and separates it from the liquid mixture. This contacting step provides a purified liquid that contains a reduced absolute amount of the free protein as compared to the absolute amount of free protein present in the liquid mixture before contact with the restricted-access media material. The purified liquid can then be collected for use or further processing. "Binding," as used herein, includes any suitable chemical or physical method or mechanism for keeping the protein with the solid phase material, such as chemical interactions, adhesion, electrostatic interactions, hydrophobic interactions, etc.

After the contacting procedure, the purified liquid preferably is collected by separating it from the restricted-access media material. Examples of suitable methods for separating the restricted-access media and the purified liquid include filtering, decanting, centrifuging, gravity draining, and gravity settling. Any suitable, known method for separating a solid or gel from a liquid can be used without departing from the invention.

Preferably, in accordance with the invention, the contacting procedure includes some suitable method to ensure adequate contact between the liquid material and the solid phase material. Contact can be enhanced by mixing or agitating the liquid mixture and the solid phase material. Another alternative method to ensure high contact includes providing a column packed with the solid phase, restricted-access media material. In this procedure, the liquid mixture, including the free protein and the conjugate and/or free polysaccharide, is introduced into the column. The liquid is then allowed to pass through the column under the force of gravity, or it is forced through the column, e.g., under vacuum or pressure.

In a more specific aspect, the invention relates to a process for producing a protein-polysaccharide conjugate, preferably a conjugate useful for a vaccine. For this production process, first a protein and a polysaccharide are reacted together under sufficient conditions to produce a liquid mixture containing a protein-polysaccharide conjugate and free protein. Any suitable protein-polysaccharide conjugation technique, including those described above for producing covalently linked protein and polysaccharide components, can be used without departing from the invention. Thereafter, the liquid mixture is contacted with a solid phase, restricted-access media material, wherein the solid phase, restricted-access media material at least partially binds with the free protein and separates it from the protein-polysaccharide conjugate. The separated protein-polysaccharide conjugate can be collected, e.g., by separating a liquid fraction including at least a portion of the protein-polysaccharide conjugate from the solid phase, restricted-access media material.

The invention further relates to protein-polysaccharide conjugates prepared by the processes described above. Such conjugates can be used as vaccines, optionally with a pharmaceutically acceptable carrier or delivery vehicle, which may include adjuvants and/or other vaccines. The invention further relates to compositions that include a protein-polysaccharide conjugate produced according to the invention in combination with a carrier (e.g., water, oils, saline, aqueous dextrose solution, aqueous glycerol solutions, etc.).

BRIEF DESCRIPTION OF THE DRAWINGS

The advantageous aspects of the invention will be more fully understood and appreciated when considered in conjunction with the following detailed description and the attached figures, wherein:

FIGS. 5A to 5C show HPLC data for samples prepared in Example 6;

FIGS. 9A and 9B depict the good recovery of high molecular weight conjugate and the selective removal of low molecular weight material, as demonstrated in Example 11.

DETAILED DESCRIPTION OF THE INVENTION

Figure 1:
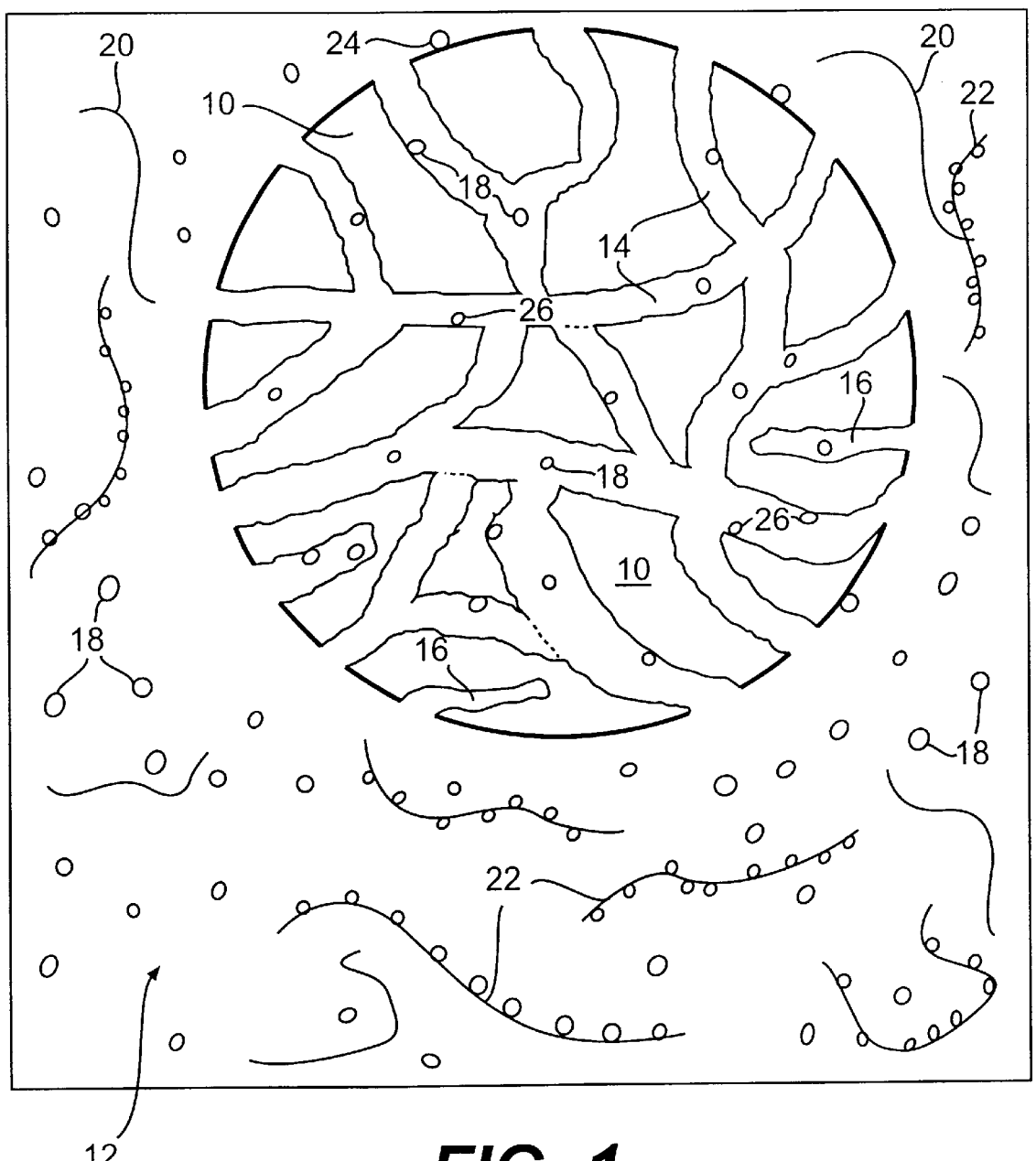
FIG. 1 schematically illustrates (not to scale) a restricted-access media particle as it is used in the process according to the invention.

The invention relates to an improved method for producing protein-polysaccharide conjugates that can be used for vaccines or immunogens. Preferably, these conjugates are immunogenic in subjects to which they are administered, thereby protecting the subject from diseases and ailments caused by various organisms (e.g., bacterial, fungal, or viral organisms).

Immunization with protein-polysaccharide conjugate vaccines can be useful to help otherwise unresponsive subjects (such as young children) mount an immune response to the polysaccharide component. For example, the use of protein-PRP conjugate vaccines has markedly reduced the incidence of *Haemophilis influenzae* type b. "PRP polysaccharide" is a capsular polysaccharide from *Haemophilis influenzae* type b.

Traditionally, conjugate vaccines have been expensive to produce, due, at least in part, to the difficult process for manufacturing them. For example, during conjugate production, typically the desired conjugate product is separated from the excess, unconjugated protein present in the reaction mixture. This separation typically is accomplished by column chromatography (e.g., size exclusion chromatography). These procedures are time consuming and expensive, and furthermore, as mentioned above, they typically result in significant loss of the conjugate product.

While it may not be absolutely necessary to remove the unconjugated protein from a conjugate vaccine to produce an immunogenic product (see, for example, U.S. patent application Ser. No. 09/003,155, filed Jan. 6, 1998 (pending), in the names of Andrew Lees and James J. Mond, entitled "Process for Preparing Conjugate Vaccines Including Free Protein and the Conjugate Vaccines, Immunogens, and Immunogenic Reagents Produced by this Process," which is entirely incorporated herein by reference), often times (e.g., for immunological or regulatory reasons), it still may be desirable to do so.

Recently, solid phase extraction materials have been developed to remove protein from DNA or RNA solutions. These extraction materials, such as StrataClean resin (available from Stratagene), bind proteins very tightly, but bind poorly to nucleic acids. See, for example, U.S. Pat. No. 4,923,978, which is entirely incorporated herein by reference. For the use described in this patent, the particle is specially treated so that nucleic acids do not bind to it, but the protein material does bind to it.

In accordance with this invention, Applicants have developed a procedure for removing unconjugated or free protein from a liquid mixture that includes a protein-polysaccharide conjugate and/or a polysaccharide component. This procedure includes contacting the liquid mixture with a solid phase, restricted-access media material, wherein the solid phase, restricted-access media material at least partially binds with the free protein and separates it from the bulk of the liquid mixture, thereby providing a purified liquid containing a reduced amount of the protein as compared to the amount of protein present in the liquid mixture prior to the contact.

After this contacting procedure, the purified liquid can be separated from the solid phase, restricted-access media material and collected.

Any suitable solid phase, restricted-access media material can be used without departing from the invention. FIG. 1 generally illustrates a solid phase particle 10 in a liquid mixture 12 used in the process according to the invention (not to scale). Generally, such solid materials 10 include pores 14 and 16 of a suitable size to allow easy access to the free protein material 18, but will significantly restrict or limit access to the larger protein-polysaccharide conjugate molecules 22. The restricted-access media material also can restrict or limit access to the unconjugated polysaccharide molecules 20, if the pore size is not too large.

The pores in the solid phase material can either interconnect with one another and/or extend completely through the solid phase particle 10, as shown by the pores at reference number 14. Alternatively, the pores can be formed as independent, stand-alone pores, as shown at reference number 16. Both types of pores 14 and 16 can be included in any given solid phase particle 10. Additionally, it is preferred that the protein materials tightly bind on the interior surface of the pores provided in the restricted-access media material (see reference number 26). Some protein material, even if part of a conjugate, can bind to the outer surface of the particle 10 (see reference number 24).

Porous silica particles are very suitable for use as the solid phase, restricted-access media material in the process of the invention, although other porous materials, such as polymer based materials (e.g., methacrylates, polystyrene, and the like) can be used without departing from the invention. Solid media materials in the form of beads (spherical or otherwise) are well suited for use in this invention. While any suitable bead size can be used without departing from the invention, an average bead size in the range of 1–50 µm has been found to be suitable, with 5–10 µm being particularly preferred.

One suitable restricted-access material that can be used according to this invention is the silica material described in U.S. Pat. No. 4,923,978 to McCormick, which patent is entirely incorporated herein by reference. While the material described in McCormick is carefully treated to remove polyvalent cationic species from the surface thereof, such cleaning steps are not necessary for the restricted-access media materials used in the process of the invention. McCormick discloses solid phase silica extraction materials with large specific surface areas of 50 $m^2/g$ or more, and preferably 100 $m^2/g$ or more. The surface area of this restricted-access media material is high because of the presence of the pores in the silica particles. The pores should be appropriately sized to allow easy entry of free protein molecules, but not so large as to allow easy entry of protein-polysaccharide molecules. In one embodiment, the pores have an effective diameter of 60 Å or greater, and an appropriate upper effective diameter limit selected so as to maintain a high specific surface area but not to allow entry of the protein-polysaccharide conjugate. Preferably, the pores of the solid materials used in the process of the invention have an effective diameter in the range of 60 Å to 500 Å, with the range of 100 Å to 300 Å being particularly preferred. One suitable, commercially available silica material for use in the process according to the invention is StrataClean™ Resin, available from Stratagene. Other commercially available silica materials that may be used in the invention include Davisil™, available from WR Grace; and Porosil™ Silica from Waters Corp. A preferred Davisil material (200–425 mesh, grade 643) has an average pore diameter of 150 Å while a preferred material from Porosil (available as product no. WAT020587) has an average pore diameter of 125 Å

Another suitable material for use in the process of the invention is found in Waters Oasis HLB extraction cartridges. This commercially available material is a solid phase extraction sorbent made of poly(divinylbenzene-co-N-vinylpyrrolidone). The commercial material has an average pore diameter of 82 Å, a specific surface area of 831 $m^2/g$, a total pore volume of 1.4 cc/g, and a mean particle diameter of 31.4 µm.

Rehydrated silica gel also can be used as the solid phase, restricted-access media material in the process according to the invention. A suitable mate rial of this type is described in Kohler, et al., *Journal of Chromatography*, Vol. 385 (1987), beginning at page 125. This article is entirely incorporated herein by reference. Another suitable solid phase, restricted-access media material for use in the invention is described in Kirkland et al., *Journal of Chromatographic Science*, Vol. 9 (1971), beginning at page 206. This article also is entirely incorporated herein by reference.

Any suitable method can be used for contacting the restricted-access media material with the liquid material containing the free protein, the protein-polysaccharide conjugate, and/or the polysaccharide. To assure good contact and separation, preferably some sort of mixing or agitating process is provided. Processing the liquid mixture with solid phase material in a batchwise manner is advantageous in some respects because it allows one to incrementally add solid phase material until the desired level of free protein is removed without excessive conjugate binding to the solid phase material. Free protein removal can be monitored between solid phase additions, for example, by HPLC. In this batch system, free protein removal can be readily monitored and controlled.

As another alternative, solid/liquid contact can be provided by introducing the liquid mixture into a column including a bed of the solid phase, restricted-access media material. The liquid can then flow through and/or around the solid phase particles in the bed, providing adequate contact to enable free protein particles to bind with the solid phase, restricted-access media materials.

An advantage of the method according to the invention is realized where the proteins bind tightly within the pores of the solid phase, restricted-access media materials, but the protein-polysaccharide conjugates do not adequately enter and/or bind within the pores. This feature of the invention, inter alia, distinguishes this invention from regular size exclusion chromatography. During size exclusion chromatography a liquid mixture is passed over a solid material that includes pores. Therefore, when the liquid sample passes over the particles, the smaller material in the mixture is capable of entering the pores, while the larger material in the mixture is partially or totally excluded from the interior pore volume. In this manner, the smaller material in the mixture has a larger effective volume available to it and through which it must pass, and thus, it elutes at a later time than the larger material. In ideal size exclusion chromatography, there is no interaction between the components and the column Matrix.

In contrast to this size exclusion chromatography procedure, in the process of the invention the protein material actually binds to the solid phase material, both inside its pores and on the outer surface thereof. This binding is believed to take place through mildly acidic hydroxyl groups on the silica or other functional groups that are present in high concentration in the solid phase materials used according to the invention. This binding holds the protein particles with the solid phase material and allows for virtually complete separation of the protein from the conjugate in a simple, rapid, and highly selective manner. Because the smaller protein molecules can bind both inside and outside the solid phase particles while the conjugate binds principally on the outside of the particles, the particles have a much higher binding capacity for the smaller protein molecules.

Selectivity for preferential binding the free protein depends on several factors, including pore size, solid phase particle size, particle surface area, the protein size, the conjugate size, and the relative size difference between the protein and the conjugate. Selectivity also depends on the ability of the solid phase material to bind with the protein. Various factors can influence the solid phase material's ability to bind, such as the pH of the liquid mixture, the presence of salts, the salt concentration, the buffer used, the temperature, etc. The skilled artisan, using routine experimentation, will be able to determine appropriate system parameters to achieve a desired degree of free protein separation.

The binding of the protein to the solid phase material may take place through one or more mechanisms, including charge and/or hydrophobic interactions. The pH, buffer, and salt concentrations should be selected so that the solid phase material is capable of binding the unconjugated protein. Selection of the proper conditions may depend on the particular solid phase material used and the protein used.

Applicants have found that the preferred pH range of the liquid mixture for binding BSA to the StrataClean silica resin is 5 to 6. The preferred liquid mixture pH range for binding tetanus toxoid protein to StrataClean silica resin is 5 to 7.4. Even outside these preferred ranges, however, the process of the invention can properly function, although it may be necessary to increase the amount of solid phase material in the system. Other restricted-access media may have other preferred buffers and pH ranges.

Further advantages of the process according to the invention over size exclusion chromatography follow. Size exclusion chromatography is known to have low capacity. Because of the ability of the solid phase material according to the invention to bind with the protein, the process according to the invention has a higher capacity than size exclusion chromatography. In other words, using a given amount of solid material, one can treat a higher volume of liquid in the process of the invention as compared to the volume treatable by a size exclusion chromatography process. As a reference, applicants have determined that StrataClean silica resin used in the process of the invention binds 10–20 mg protein per ml of the StrataClean solution.

Additionally, size exclusion chromatography is a slow process, whereas the solid phase treatment process according to the invention is quite rapid. Size exclusion chromatography must be conducted in a column, and these columns typically are quite difficult to pack (particularly for larger columns). The solid phase treatment method according to the invention, on the other hand, does not require a column, although one can be used, if desired. Thus, the invention avoids the requirement of an expensive column and matrix necessary for size exclusion chromatography. Another advantage of the method according to the invention relates to clean-up. Because the solid phase material used in the invention is relatively inexpensive, it can be discarded after use. This avoids the expensive clean-up and validating procedure needed before each use of a size exclusion chromatography column for GMP. As noted above, under good manufacturing procedure guidelines, when using size exclusion chromatography, a separate and dedicated column is needed for each vaccine.

Another advantage of the method according to the invention is realized in that it allows free protein to be removed from both dilute and concentrated solutions of a conjugate vaccine. Typical gel filtration columns, when used to remove free protein from protein-polysaccharide conjugates, must be loaded with sample volumes that are less than 10% (by volume) of the column volume. Furthermore, gel filtration typically dilutes the sample at least 3-fold. These further dilutions can render the conjugate too dilute for practical use and separation, particularly if the original liquid sample is already quite dilute. At the very least, these additional dilutions can necessitate later concentration steps, thereby adding to the cost and time involved in conjugate preparation. The process according to the invention is not hampered by these dilution limitations and requirements.

Removing the free protein from a conjugate also can be advantageous because it can facilitate further processing of the conjugate. For example, after the free protein is removed, the purified liquid mixture including the conjugate can be further processed to remove the free polysaccharide. Because the process of the invention does not significantly dilute the liquid mixture, as described above, it can make further processing of the conjugate proceed more easily.

In the process according to the invention, several characteristics of the system can be adjusted to optimize free protein removal and conjugate recovery. These characteristics include: overall volume of the solid phase, restricted-access media material; pore volume; pore size; and solid phase material exterior surface area. Because the protein present as part of a conjugate also can bind to the restricted-access media material (particularly on its outer surface), to minimize conjugate loss, preferably one will select solid phase materials having a maximum interior pore volume while keeping the exterior bead surface area at a minimum. Additionally, using an excessively large overall volume of restricted-access media material will result in excess conjugate loss because a large outer surface area will be available on which the protein of the conjugate can bind. When small overall volumes of restricted-access media materials are used, the free protein and the conjugated protein compete for binding sites on the solid bead exterior, producing better separation and higher conjugate yields. Excessively large pore sizes can allow the conjugate to enter the bead interior, resulting in conjugate loss, and tends to reduce the interior pore volume. Excessively small pore sizes can adversely affect separation and selectivity if the free protein does not readily enter the pores of the solid phase material. The skilled artisan, using routine experimentation, will be capable of selecting the proper combination of these and other parameters to remove the desired amount of free protein without excessively binding and losing protein-polysaccharide conjugate product. This is shown, for example, in FIG. 6, which is described in more detail below.

The term "polysaccharide," as used in this application, includes any polysaccharide, such as dextran, carboxylated dextran (such as carboxymethyl dextran), the polysaccharides of biologically relevant bacteria, such as *Neisseria meningiditis* polysaccharide type C ("Neisseria PsC"), Pneumococcal polysaccharides (such as Pn14, Pn6, Pn19, and Pn23), and a capsular polysaccharide from *Haemophilis influenzae* type b ("PRP polysaccharide"). The various polysaccharides described in the above-noted patents and patent applications of Dr. Andrew Lees also can be used in this invention.

The term "protein," as used in this application, includes proteins, peptides, haptens, and lipoproteins. Specific examples include bovine serum albumin ("BSA"), tetanus toxoid, diptheria toxoid, pertussis toxoid, Rib protein, intimin, gD protein, LHRH peptide, CFA/I consensus peptide (see F. J. Cassels, et al., *Journal of Industrial Microbiology*, 1996 Annual Meeting for the Society of Industrial Microbiology), lipoOspA, lipoD, PamCys, and monophosphorolipid A. The various proteins described in the above-noted patents and patent applications of Dr. Andrew Lees also can be used in this invention. The term "free protein" means unreacted protein or unconjugated protein that is not covalently linked to a polysaccharide molecule. A "free protein" includes both unmodified proteins and derivatized or functionalized proteins that may be present in the conjugation reaction mixture.

The following Examples are provided to more specifically illustrate the invention. These examples should be construed as illustrating the invention, and not as limiting it. The following information also will help one more fully understand the examples that follow.

Unless otherwise noted, "HEPES buffer" (or "HE buffer"), as used in this application, represents a mixture of 0.15 M hydroxyethyl piperazine N'-2-ethane sulfonic acid ("HEPES") and 2 mM ethylenediaminetetraacetate ("EDTA") to provide a solution having a pH of 7.3. Similarly, unless otherwise noted, "HEPES" refers to HEPES alone, without EDTA (pH=8). "Saline" represents a 0.15 M solution of NaCl in water.

In the examples that follow, certain examples use bovine serum albumin ("BSA") as a model protein and/or dextran as a model polysaccharide. Of course, biologically relevant proteins and polysaccharides also can be used in the practice of the invention. Specific examples including biologically relevant proteins and polysaccharides also are included in this application.

The monomeric BSA used in these examples was prepared from Intergen low endotoxin BSA (from Intergen Corp.) by brief treatment with 10 mM iodoacetamide in HEPES buffer at pH 7.3, and then gel filtration on a 2.5×100 cm S100HR column (from Pharmacia) as described in Lees, et al., *Vaccine*, Vol. 14, No. 3, (1996) pp. 190–198 (described above).

When determined in the examples that follow, the concentration of polysaccharides was determined using the resorcinol/sulfuric acid method of Monsigny, et al., *Anal. Chem.* Vol. 175, pg. 525 (1988), using the relevant polysaccharide standard. The concentration of protein was determined using the Coomassie Plus Protein Assay Reagent (available from Pierce Chemical Co., of Rockport, Ill.) (an appropriate protein, such as BSA or tetanus toxoid, was used as the standard). The Monsigny article is entirely incorporated herein by reference. Size exclusion high performance liquid chromatography (i.e., the HPLC runs described in the examples that follow) was conducted on a Phenomenex BioSep SEC3000 column. The HPLC runs were monitored with a Waters 486 UV detector at 280 nm.

EXAMPLE 1

This first example illustrates removal of unconjugated or free tetanus toxoid protein from a reaction mixture including a tetanus toxoid-Pneumococcal 14 conjugate ("TT-Pn14"). First, the TT-Pn14 conjugate was prepared by a standard method using CDAP cyanylating reagent to provide a liquid reaction mixture containing the conjugate as well as free tetanus toxoid protein in saline (pH of about 6). This conjugate was prepared in the general manner described in Lees, et al., *Vaccine*, Vol. 14, No. 3 (1996), pp. 190–198, discussed above. Thereafter, the liquid mixture was divided into two 25 µl portions. One 25 µl portion was treated in a process according to the invention by mixing it with 10 µl of solid phase StrataClean silica resin (available from Stratagene) ("Sample B"), and the other portion was not treated with StrataClean silica resin ("Sample A"). Each sample was incubated for 20 minutes with mixing. The samples then were passed through a Millipore Ultrafree MC 0.45 micron filter to separate the liquid from any solid materials present.

Figure 2:
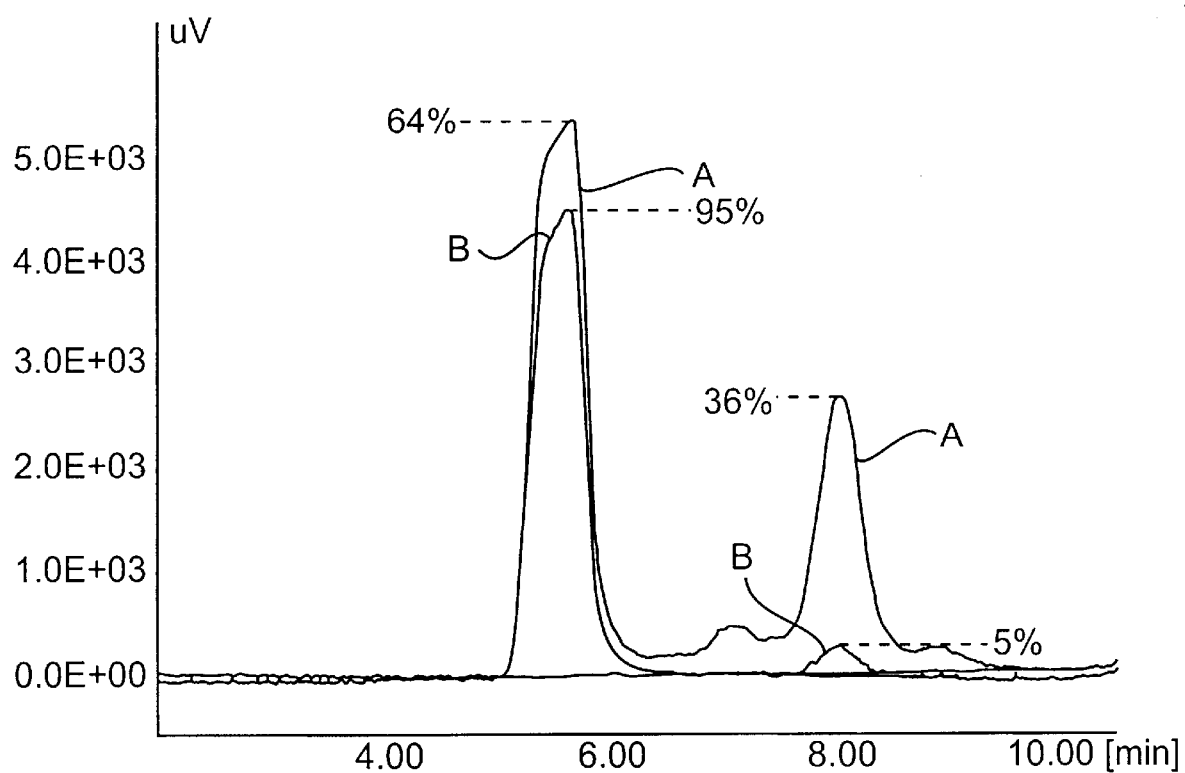
FIG. 2 shows high performance liquid chromatography ("HPLC") data for samples prepared in Example 1.

The silica resin was then rinsed with buffer, and enough buffer was added to each sample to increase its volume to 100 µl. 50 µl of each sample was analyzed by size exclusion HPLC on a Phenomenex BioSep SEC3000 column, equilibrated with 0.1 M potassium phosphate buffer ("KPO$_4$", pH 7.3), at a rate of 1 ml/minute. The HPLC results are shown in FIG. 2. For Sample A, which did not include treatment with the StrataClean silica resin, the resulting liquid material contained 36% free tetanus toxoid protein (the low molecular weight peak at about 8 minutes) and 64% TT-Pn14 conjugate (the high molecular weight peak at about 5.5 minutes). The liquid sample purified by the process according to the invention (Sample B), however, contained 95% TT-Pn14 conjugate and 5% free protein. Based on the area under the high molecular weight peaks, it was determined that the recovery of conjugate material in Sample B was 76%.

Thus, this example shows that the method according to the invention can be used to easily and effectively separate free protein from a reaction mixture including a protein-polysaccharide conjugate and free protein.

EXAMPLE 2

This example shows the effect of using different amounts of restricted-access media material during the separation process. A TT-Pn14 conjugate was prepared using CDAP coupling, by a known procedure as described in the patents and patent applications described above. The resulting liquid reaction mixture included both the conjugate and free tetanus toxoid protein. After dialysis into phosphate buffered saline ("PBS"; a pH of about 7.4), 100 µl samples of the liquid reaction mixture were processed with 0, 5, or 20 µl of the StrataClean silica resin in the same manner described in Example 1, to provide purified liquid samples. After this processing, the samples were analyzed by size exclusion HPLC in the manner described in Example 1, and the following results were obtained.

TABLE 1

| Resin Amount | High MW Area* | Low MW Area** | % Free Protein | % Recovery of the HMW Conjugate*** |
|---|---|---|---|---|
| 0 µl | 384,726 | 289,248 | 42.9% | 100% |
| 5 µl | 300,566 | 75,884 | 20.2% | 82% |
| 20 µl | 236,865 | 4,265 | 1.8% | 73.9% |

*Corresponds to the amount of conjugate.
**Corresponds to the amount of free protein.
***After correcting for dilution. Based on the amount of conjugate recovered when 0 µl of silica resin was used for the treatment.

From this example, one can see that it is a matter of routine experimentation to determine the amount of restricted-access media material needed to reduce the free protein content of the liquid reaction mixture to a desired level. Additionally, while the percent recovery data indicates that some conjugate material is lost during the process according to the invention (e.g., by binding to the outer bead surface), the unconjugated free protein material is adsorbed preferentially on and/or in the solid phase resin material.

EXAMPLE 3

In this example, free protein removal using the process according to the invention was directly compared with its removal using gel filtration. A TT-Pn14 conjugate was made as described above in Example 2, using CDAP coupling, and the reaction mixture was dialyzed into PBS (pH of about 7.4). The resulting material was a liquid mixture (Sample A) containing both free protein and the protein-polysaccharide conjugate.

One portion of this mixture was treated with 75 µl of StrataClean silica resin for one hour on a rotator. The sample (Sample B) was then centrifuged and the supernatant removed. The resin was washed twice with 100 µl of saline.

To prepare a sample using the known gel filtration method for removing free protein from a conjugate (Sample C), a second portion of this liquid mixture was passed over a 1×60 S400HR gel filtration column, and the high molecular weight fractions were pooled.

Figure 3A:
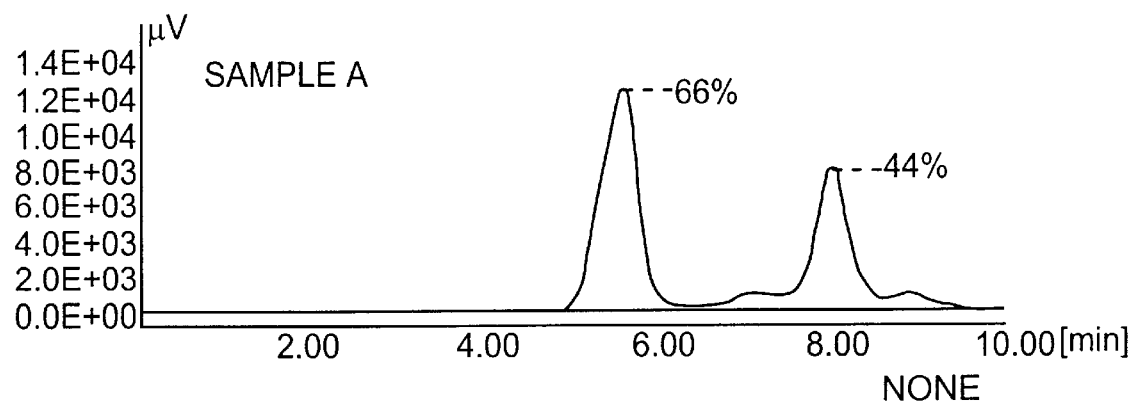
FIGS. 3A and 3B show HPLC data for samples prepared in Example 3.
Figure 3B:
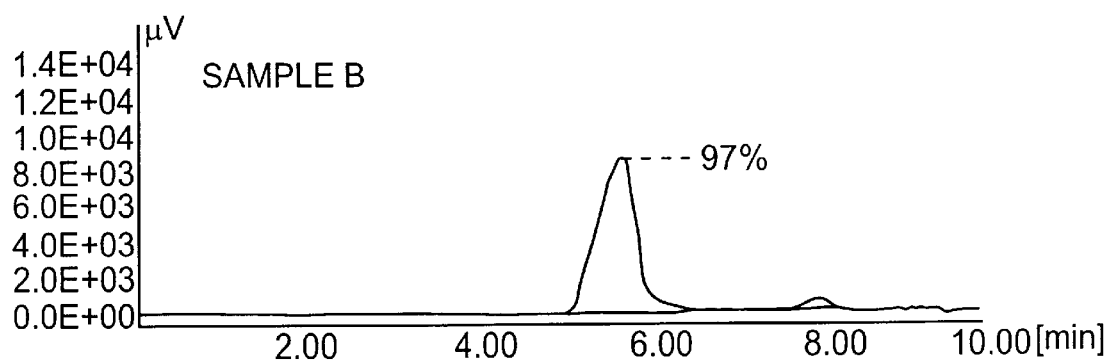

The three samples then were analyzed by size exclusion HPLC to determine the amount of free protein present with the conjugates. FIG. 3A shows the HPLC for Sample A, subjected only to the dialysis treatment. The HPLC shows a high amount of the protein component present (represented by the low molecular weight peak at about 8 minutes, corresponding to 44% of the area under the curve). After treatment with the StrataClean silica resin, however, as shown in FIG. 3B, most of this protein has been removed from the liquid mixture. FIG. 3B shows the HPLC data, and notably, the component eluting at about 8 minutes contains about 3% of the area under the curve, indicating a significant reduction in the amount of free protein present in the liquid mixture.

The protein content for each sample was determined using a Coomassie Plus Assay (available from Pierce), and the polysaccharide content was determined using the resorcinol method described above. The results are shown in Table 2 below:

TABLE 2

| Sample | Brief Description | mg TT/mg Pn14 | % Ps Recovery* |
|---|---|---|---|
| Sample A | Dialysis only | 1.7 mg/mg | 100% |
| Sample B | StrataClean Silica Resin Treatment | 0.44 mg/mg | >95% |
| Sample C | Gel Filtration Treatment | 0.44 mg/mg | 71% |

*Percent polysaccharide ("Ps") recovery, using Sample A as the base.

From this data, one can see that the use of the StrataClean silica resin, in accordance with the process of the invention, produced a conjugate having a similar protein-polysaccharide ratio as did the process using the more tedious gel filtration procedure. The process according to the invention, however, provided a much higher recovery of the polysaccharide component (>95%) as compared to the gel filtration procedure (71%). These findings agree with known experiences relating to gel filtration, where significant loss of the conjugate product has been observed.

Thus, this example demonstrates that the process according to the invention can be used to effectively remove the free protein component from a liquid mixture including free protein and a protein-polysaccharide conjugate, while still allowing an excellent recovery of the conjugate product.

EXAMPLE 4

This example describes use of the method of the invention on a product containing a different polysaccharide component prepared using a different coupling chemistry. Additionally, this example shows the effect of increasing the amount of restricted-access media material on the free protein removal efficiency in the process of the invention.

Tetanus toxoid protein was coupled to *Neisseria meningiditis* polysaccharide type C ("PsC") using N-succinimidyl iodoacetate ("SIA") coupling, in the general manner described in U.S. Provisional Patent Appln. No. 60/042,379 (filed Apr. 24, 1997). Neisseria PsC is a charged polysaccharide, and in this way, it differs from the Pneumococcal 14 polysaccharides used in the examples above. After the conjugation reaction was completed, the resulting liquid reaction mixture contained both free tetanus toxoid protein and a TT/PsC conjugate in PBS (pH of about 7.4).

In performing the process according to the invention, 50 µl samples of the liquid reaction mixture (containing both free protein and conjugate) were mixed with varying amounts of StrataClean silica resin in an Ultrafree MC 0.45 µm filter device. These mixtures were incubated for 10 minutes on a rotator and then centrifuged, and then the samples were analyzed by HPLC. The HPLC test results shown in Table 3 were obtained. In Table 3 (and throughout this application), "HMW" stands for the "High Molecular Weight" component, which, in this instance, corresponds to the TT/PsC conjugate. Throughout this application, "LMW" stands for the "Low Molecular Weight" component, the free tetanus toxoid protein, in this example. The percent of the high molecular weight component is determined based on the amount of conjugate recovered without using the Strata-Clean silica resin treatment process according to the invention (i.e., 0 μl resin).

TABLE 3

| Silica Resin Amount | HMW Peak Area | LMW Peak Area | % Free Protein | % HMW Component Recovered* |
|---|---|---|---|---|
| 0 μl | 231,140 | 493,878 | 68.1% | 100% |
| 1.25 μl | 238,462 | 112,491 | 32.1% | 103% |
| 2.5 μl | 90,298 | 32,772 | 14.7% | 82.3% |
| 5 μl | 168,387 | 18,274 | 9.8% | 72.8% |

*Using the treatment with 0 μl silica resin as the base.

This example demonstrates that the process according to the invention can be used to produce a desired separation of free protein from a conjugate, while still producing suitable conjugate yields, even in situations where the free protein traditionally has been difficult to separate from the conjugate. As expected, increasing amounts of silica resin results in increasing free protein removal, which must be balanced against the loss of high molecular weight conjugate material.

EXAMPLE 5

In this example, the "kinetics" of the process according to the invention was investigated. Specifically, experiments were conducted to determine the restricted-access media treatment time necessary to produce a desired level of free protein separation in the process according to the invention.

A BSA/dextran conjugate was produced as follows. First, 1 ml of T2000 dextran (available from Pharmacia), at 10 mg dextran/ml in saline, was mixed with 50 μl of 100 mg/ml CDAP in acetonitrile. Thirty seconds later, 50 μl of 0.2 M triethylamine was added, and an additional thirty seconds later, an additional 50 μl of 0.2 M triethylamine was added. After an additional 1.5 minutes, 1 ml of monomeric BSA solution was added (the BSA was present at a concentration of 10 mg/ml in 0.4 M HEPES (pH 8)). The reaction was allowed to proceed at room temperature.

After 3 hours, the reaction was quenched by adding 200 μl of 1 M glycine. This mixture was allowed to stand overnight at 4° C. The next day, the reaction mixture was dialyzed into saline plus azide to produce a liquid reaction mixture that included free BSA protein along with a BSA/dextran conjugate (pH of about 6). Using HPLC, it was determined that this reaction mixture contained 43% free BSA protein (based on the area under the LMW peak).

50 μl of the liquid mixture then was treated with 10 μl of StrataClean silica resin in an Ultrafree MC 0.45 μm filter device, and incubated and mixed on a rotator. Samples were taken at various times during this mixing process, and the amount of free protein present was determined using HPLC as above. The test results are shown in FIG. 4.

Figure 4:
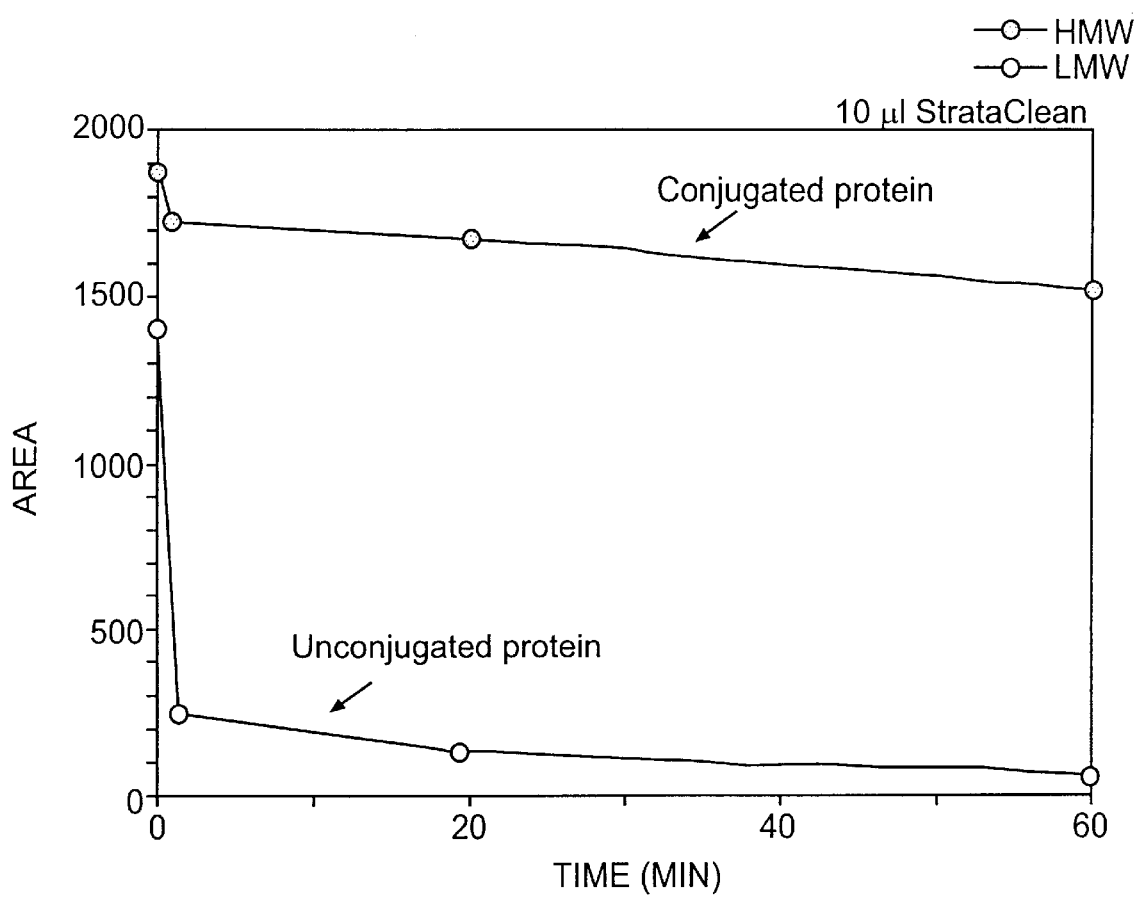
FIG. 4 shows kinetic data for the conjugate/free protein separation conducted in Example 5.

FIG. 4 shows that the amount of unconjugated protein (BSA, the low molecular weight component) rapidly drops as compared to the amount of the high molecular weight component that includes the conjugated protein (the BSA/dextran conjugate). This data indicates that the restricted-access media material used in the process according to the invention preferentially and rapidly removes the unconjugated, free protein from the liquid reaction mixture. In this instance, treatment times of less than 20 minutes were adequate to remove a major amount of the free protein from the reaction mixture.

EXAMPLE 6

For this example, a tetanus toxoid protein was coupled to a capsular polysaccharide from *Haemophilis influenzae* type b ("PRP polysaccharide") using CDAP as a coupling reagent. PRP polysaccharide is a negatively charged, high molecular weight polysaccharide. The resulting liquid reaction mixture included free tetanus toxoid protein along with a TT/PRP conjugate in PBS (pH of about 7.4).

To provide a standard (Sample A), the liquid mixture was passed through an S400HR gel filtration column to remove the free protein. The HPLC of this sample is shown in FIG. 5A. This conjugate was found to contain 0.21 mg/ml tetanus toxoid and 0.31 mg/ml PRP (which corresponds to 0.68 mg TT/mg PRP).

100 μl of conjugate Sample A was "spiked" by adding 45 ul of 1 mg/ml tetanus toxoid protein. An HPLC of this material, Sample B, was conducted, and the HPLC results are shown in FIG. 5B.

50 μl of spiked Sample B was then treated with 7.5 μl of StrataClean silica resin for 10 minutes on a rotator according to the process of the invention. The treated material, Sample C, then was filtered, and an HPLC conducted with the results shown in FIG. 5C.

The test results shown in FIGS. 5A through 5C are summarized in Table 4 as follows:

TABLE 4

| Sample | HMW Area | LWM Area | % HMW Component Recovered** |
|---|---|---|---|
| Sample A (Standard) | 339,685* | 0 | 100% |
| Sample B (Spiked Conjugate) | 337,767 | 575,876 | 99.4% |
| Sample C (Resin Treated Conjugate) | 338,170 | 0 | 99.5% |

*Area shown in FIG. 5A corrected for dilution after addition of free tetanus toxoid. This correction corresponds to the original area shown in FIG. 5A × 100 μl (original volume)/145 μl (diluted volume) or 478044 × 100/145 = 339,685.
**Using the HMW area of Sample A as the base.

This example demonstrates that a large excess of unconjugated tetanus toxoid protein can be removed in the process according to the invention with essentially quantitative recovery of the conjugate. As the data shows, essentially 100% of the free protein was removed using the process according to the invention, and yet, essentially 100% of the high molecular weight conjugate material was recovered.

EXAMPLE 7

This example describes the use of restricted-access media materials other than StrataClean silica resin in the process according to the invention. In neither of these experiments was an effort made to optimize recovery. These experiments were performed to show that protein removal selectivity can be accomplished using these restricted-access medium materials.

Experiment 7A

For this experiment, the solid poly(divinylbenzene-co-N-vinylpyrrolidone) material of a Waters Oasis extraction cartridge (Waters Part No. 94225) was used as the restricted-access media material. For preparation, the cartridge was rinsed sequentially with 2 ml of methanol, 2 ml water, and 2 ml saline.

To test the effectiveness of the cartridge in the process of the invention, a TT/Pn14 conjugate was produced using CDAP coupling reagent, thereby providing a liquid mixture containing the TT/Pn14 conjugate and free tetanus toxoid protein in PBS (pH of about 7.4). An HPLC analysis was conducted on this mixture.

Then, to purify the liquid mixture, it was drawn through the Oasis extraction cartridge, treated as above, using a syringe. The cartridge was then rinsed with saline (50 to 100 µl). The resulting liquid also was analyzed by HPLC. As a comparative standard, an HPLC analysis also was conducted on a saline sample. The HPLC results are as follows:

TABLE 5

| Sample | HMW Area | LMW Area | % LMW Component | % Recovery of the HMW Component* |
|---|---|---|---|---|
| Conjugate plus free protein | 385,700 | 288,256 | 43% | 100% |
| Conjugate plus Oasis treatment | 235,101** | 0 | 0% | 61% |
| Saline only | 0 | 0 | — | — |

*Using the untreated liquid mixture (conjugate plus free protein) as the base.
**Area corrected for dilution.

This data demonstrates that selectivity for free protein removal can be realized using the solid material from a Waters Oasis extraction cartridge.

Experiment 7B

For this experiment, the restricted access-media material was provided by cutting apart a SepPack silica cartridge (Waters Part No. 51900), removing the silica material, and suspending it in saline at 150 mg/ml to form a silica hydrate. 50 µl of this suspension was added to 50 µl of a liquid mixture including free protein and a BSA/dextran conjugate in saline (pH of about 6), produced using CDAP chemistry. The liquid mixture and the silica suspension were mixed on a rotator for 10 minutes in one experiment and for 25 minutes in another experiment. The purified liquid materials resulting from these experiments were analyzed by HPLC.

Additionally, as a standard, prior to treatment with the SepPack silica material, a sample of the original liquid mixture (conjugate plus free protein) was analyzed by HPLC. The HPLC test results are provided in the following table:

TABLE 6

| Sample | HMW Area | LMW Area | % LMW Component | % Recovery of the HMW Component* |
|---|---|---|---|---|
| Conjugate plus free protein | 1,378,134 | 562,748 | 29% | 100% |
| Conjugate plus 10 min. silica treatment | 685,757 | 99,945 | 13% | 49.8% |
| Conjugate plus 25 min. silica treatment | 592,903 | 18,659 | 3% | 43% |

*Using the untreated sample (conjugate plus free protein) as the base.

Again, this data shows selectivity for free protein removal can be realized using SepPack silica in suspension as a restricted-access media material.

EXAMPLE 8

This example describes the effectiveness of the process according to the invention for use on different size polysaccharide components using different types of restricted-access media materials.

Two different BSA/dextran conjugates were prepared under identical conditions using CDAP coupling. One conjugate was prepared using a fractionated 40 kDa dextran polysaccharide, and the other included a fractionated 2000 kDa dextran polysaccharide. A third conjugate was prepared using half as much BSA in the coupling reaction ("low BSA content"). An HPLC analysis of each liquid reaction mixture was performed.

The reaction mixtures including the conjugates and free protein in saline (pH of about 6) were then treated either with a StrataClean silica resin or a Waters Oasis solid phase material (poly(divinylbenzene-co-N-vinylpyrrolidone) including a synthetic surface containing a hydrophobic binding surface). The recovered material was analyzed to determine the recovery of the high molecular weight component (the conjugate) and for the amount of the residual low molecular weight component (the free protein). The results are shown in Table 7 which follows:

TABLE 7

| Conjugate/Treatment | % HMW | % LMW | % Recovery HMW* |
|---|---|---|---|
| 40 kDa dextran/no purifying treatment | 46% | 54% | 100%* |
| 40 kDa dextran/StrataClean | 63% | 37% | 42% |
| 40 kDa dextran/Oasis | 61% | 39% | 44% |
| 2000 kDa dextran/no purifying treatment | 54% | 43% | 100%* |
| 2000 kDa dextran/StrataClean | 74% | 26% | 96% |
| 2000 kDa dextran - low BSA content/no purifying treatment | 71% | 29% | 100%* |
| 2000 kDa dextran - low BSA content/Oasis | 98% | 2% | 75% |

*Using the respective unpurified samples as the base.

This data indicates that in the methods according to the invention, the selectivity for absorbing the LMW protein component over the HMW conjugate component increases with increasing molecular weight of the high molecular weight component. Relatively low selectivity was realized with the 40 kDa dextran polysaccharide samples as compared to the selectivity when the 2000 kDa dextran polysaccharide was used. This data indicates that the process according to the invention acts, at least in part, by restricting access of the larger, high molecular weight components from the interior or pores of the restricted-access media material. Much less conjugate is adsorbed by the solid phase material when the high molecular weight component is large enough to be excluded from the pores in the solid material.

Figure 6:
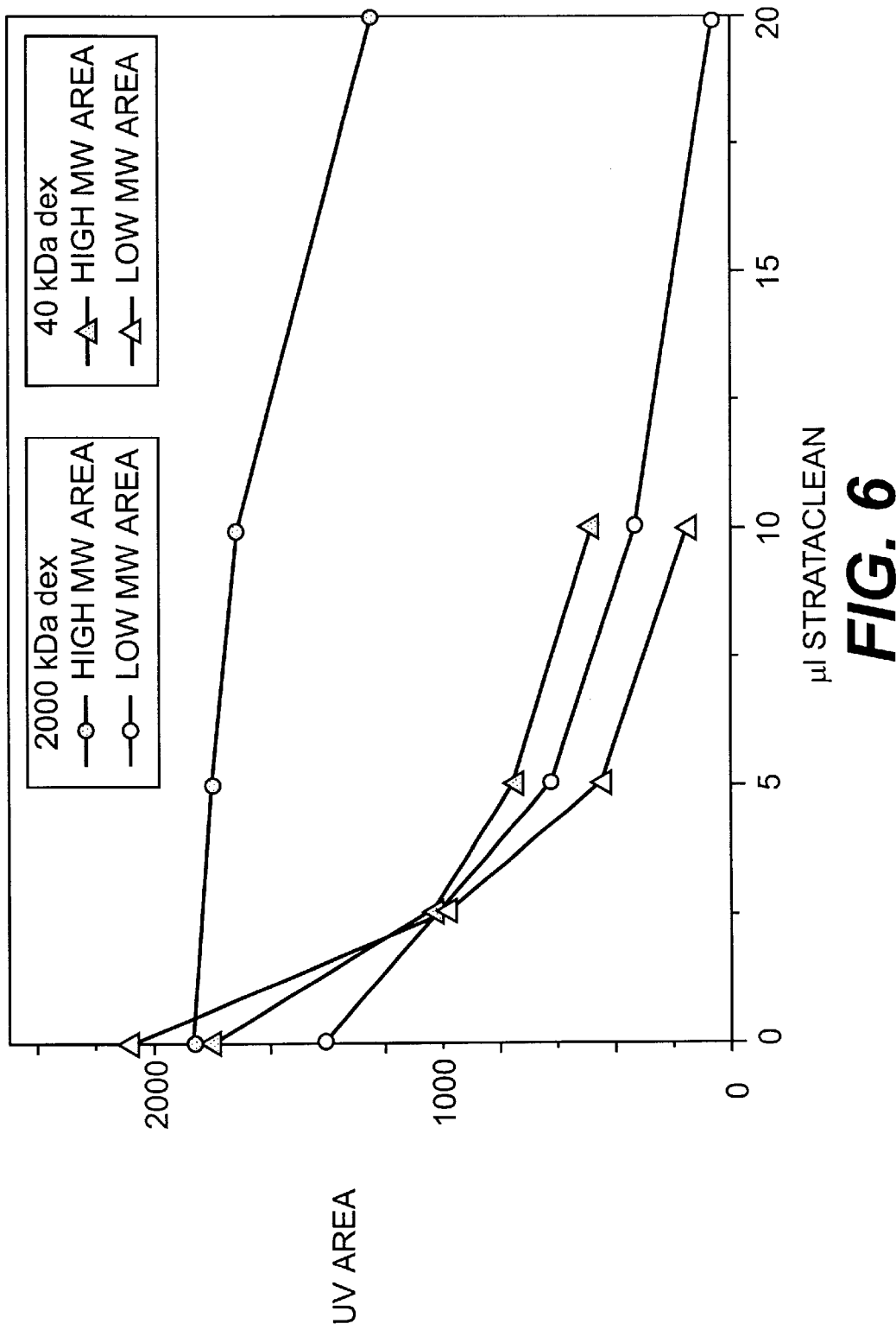
FIG. 6 relates to Example 8 and illustrates that the selectivity of the restricted-access media material used in the process of the invention is, at least in part, dependent on the molecular weight of the conjugate.

The graph of FIG. 6 confirms these observations. In FIG. 6, the area under the HPLC curve corresponding to the high and low molecular weight components is graphed as a function of the amount of StrataClean silica resin used in the treatment procedure. As can be seen, for the high molecular weight 2000 kDa dextran, a very pronounced difference in absorption of the high and low molecular weight components is observed. A smaller difference in absorption by the resin is observed when the polysaccharide has a lower molecular weight (the 40 kDa dextran).

EXAMPLE 9

This example demonstrates that the purified protein-polysaccharide conjugates produced according to the invention produce an antibody response to the polysaccharide component when used in a vaccine.

Experiment 9A

For this experiment, a batch of a TT/Pn14 conjugate was prepared by a known method, and the free protein was removed from one portion of the conjugate using a standard gel filtration method, and the free protein was removed from another portion of the conjugate using a StrataClean silica restricted-access media material according to the invention. Thus, the conjugates used in this experiment were prepared from a common batch ("matched conjugates"), but the purification technique differed.

Eight mice were immunized with 2.5 µg of Pn14 present in the above-noted TT/Pn14 conjugates on Day 0. A booster immunization with the same immunogen was given on Day 14. Four of the animals were immunized with the conjugate purified by the gel filtration technique, and four were immunized with the conjugate purified using the StrataClean silica restricted-access media material according to the invention. The animals were bled on Day 28, and an anti-Pn14 IgG response was measured by ELISA ("enzyme-linked immunosorbent assay"), OD at 1:1000. The average ELISA adsorbance for the four animals treated with the immunogen purified by the gel filtration protocol was 0.576±0.145 ($\bar{x}$±standard deviation), and the average ELISA adsorbance the four animals treated with the immunogen purified by the restricted-access media protocol was 0.381±0.075 ($\bar{x}$±standard deviation). While the gel filtration protocol induced somewhat higher antibody levels in most animals, there was no statistical difference between the two protocols (using Student's T test with one tail at a 99% confidence level). Each conjugate type induced an acceptable polysaccharide antibody response in the animals.

Experiment 9B

This experiment was performed to test the anti-body response to a Neisseria PsC polysaccharide. TT/PsC conjugates were prepared separately (i.e., not "matched conjugates" as described above), and one conjugate was purified using gel filtration and the other conjugate was purified using the restricted-access media protocol according to the invention. The immunization protocol from Experiment 9A was repeated, using different mice injected with one of the TT/PsC conjugates. The ELISA test results (ELISA OD at 1:1000) were as follows: the average ELISA adsorbance for the four animals treated with the immunogen purified by the gel filtration protocol was 1.006±0.323 ($\bar{x}$±standard deviation), and the average ELISA adsorbance for the four animals treated with the immunogen purified by the restricted-access media protocol was 0.662±0.361 ($\bar{x}$±standard deviation). Again, this data demonstrates that the procedure according to the invention produces conjugates that induce an acceptable immune response to the polysaccharide component in animals. No statistical difference is seen between these two protocols in this experiment (using Student's T test with one tail at a 99% confidence level).

EXAMPLE 10

Experiment 10A

This example compares selective adsorption between solid bead and porous beads and demonstrates that solid beads do not permit selective adsorption.

Figure 7:
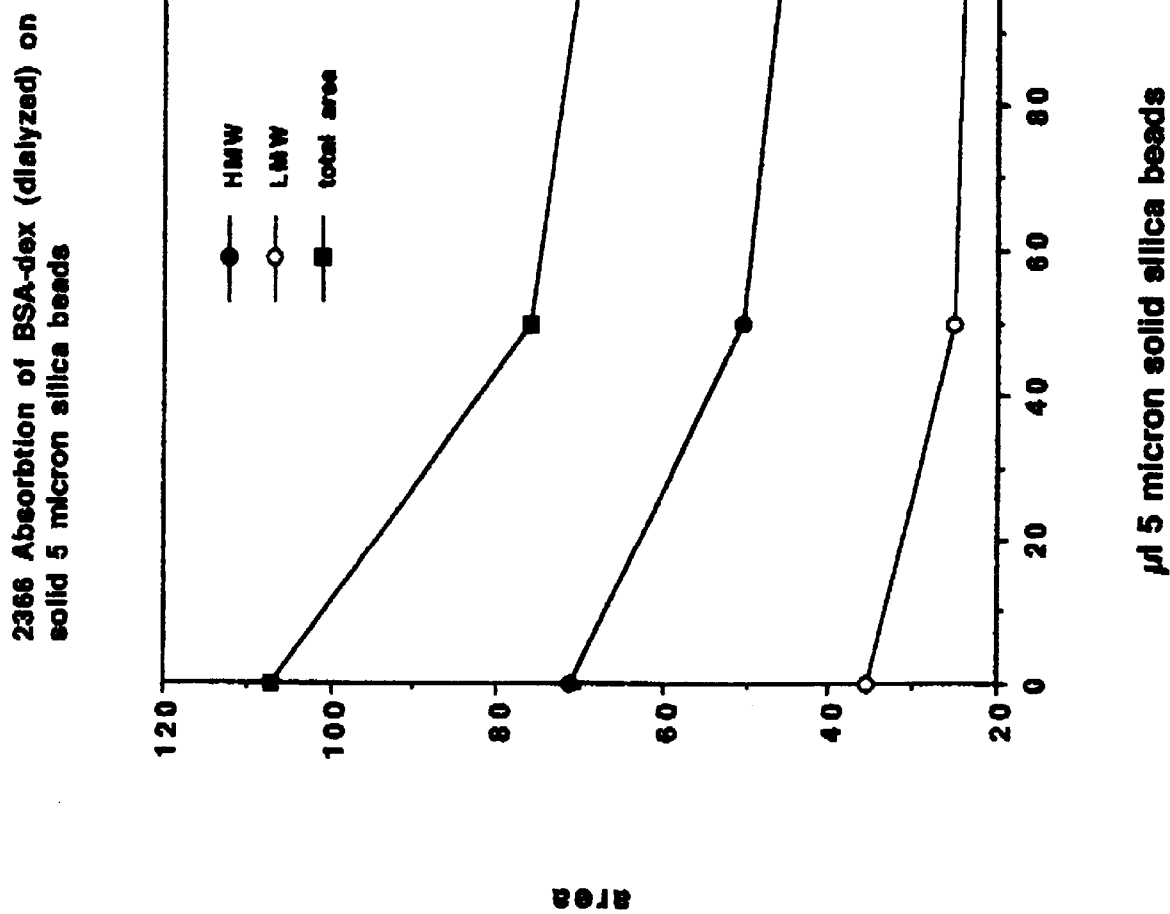
FIG. 7 demonstrates there was no selective adsorption of the unconjugated protein with the nonporous silica beads, in contrast to the porous silica, as set forth in Example 10, Experiment 10A.

As set forth above in Example 5, BSA was covalently linked to CDAP activated high molecular weight T2000 dextran and dialyzed into saline. 50 µl of 4 M NaCl was added to 50 µl of the conjugate solution and mixed with 0–100 µl of a 10% solution of 5µ solid silica beads (Bangs Laboratories product #S0050004PN). After 5 minutes, the solution was filtered through an Ultrafree MC device (Millipore) and analyzed by SEC HPLC, as noted above. The adsorption peaks are set forth in FIG. 7, in which HMW indicates the area of the high molecular weight peak (conjugate) and LMW indicates the area of the unconjugated protein. As the Figure demonstrates, there was no selective adsorption of the unconjugated protein with the solid beads, in contrast to the porous silica.

Experiment 10B

The importance of pore size is further illustrated in this example. BSA-dextran conjugates were prepared as set forth above and in Example 5, and then dialyzed to yield both free BSA protein along with a BSA/dextran conjugate. 25 µl of the BSA-dex conjugate solution was treated with 25 µl of 5µ silica of 60, 100 or 500 Å pore size (Lichrosphere Si, HPLC grade, available from EM Merck) suspended at 500 mg/ml in deionized water. After ten minutes, the samples were filtered in an Ultrafree MC device to remove the silica and then assayed by SEC HPLC. Selectivity is measured as the % decrease in the area of the monomer peak divided by the % decrease in the area of the high molecular weight peak. Pore size 0 used 5µ solid silica from Bangs Laboratories, as described above in Experiment 10A.

Figure 8:
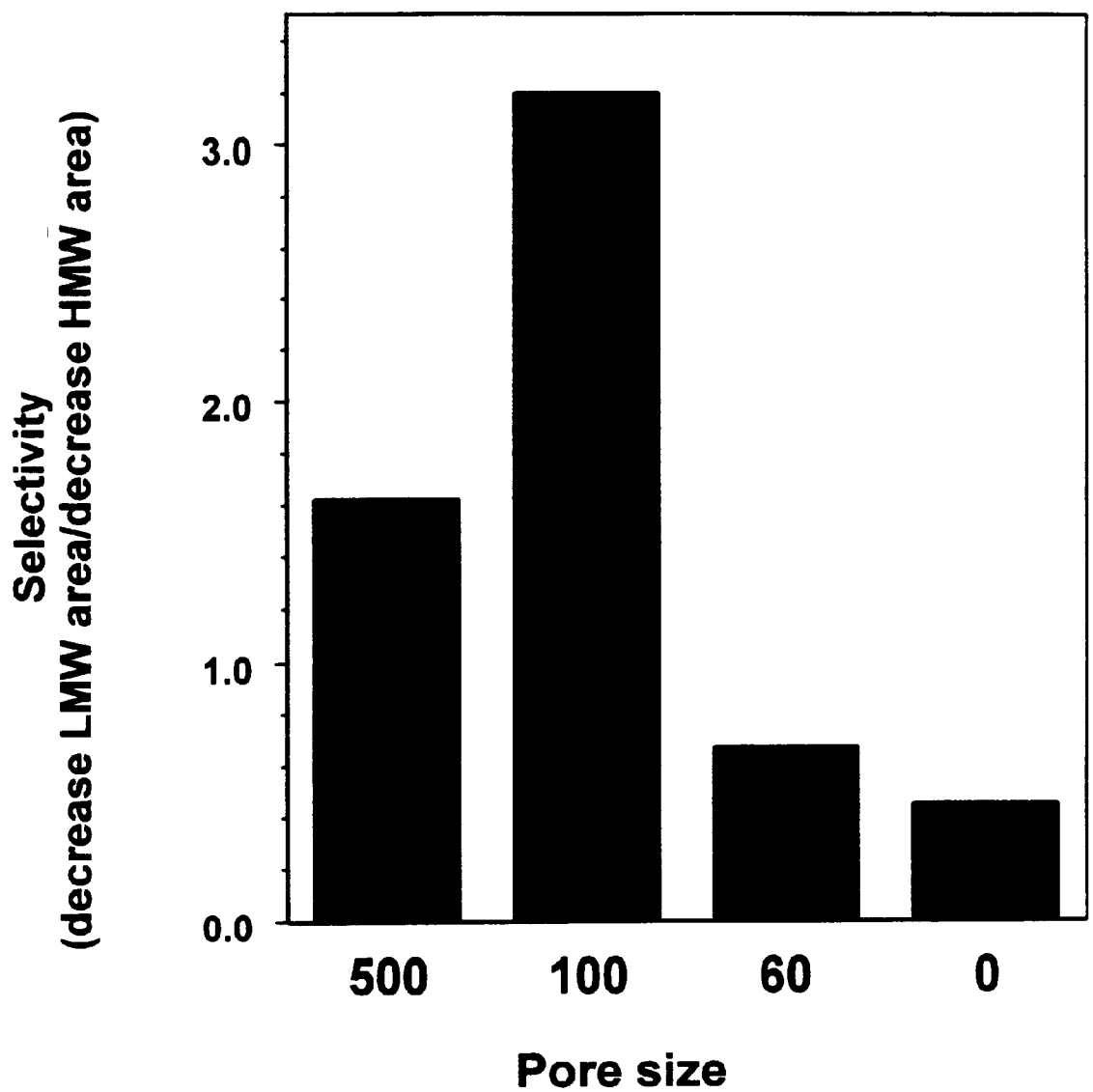
FIG. 8, from Example 10, Experiment 10B, illustrates the effect of pore size on selective adsorption.

As set forth below in FIG. 8, there was no preferential binding of the monomer for solid silica particles or for silica with 60 Å pores. Furthermore, the area of the high and low MW peaks decreased only slightly, suggesting that there was only binding to the exterior of the particles. Maximum selectivity was obtained for the 100 Å pore size. Selectivity decreased for the largest pore size, possibly because the conjugates began to enter the pores.

It was not possible to directly compare absolute amounts of binding because the total surface area varied, depending on the pore size (60 Å=650 m$^2$/g; 100 Å=420 m$^2$/g; 500 Å=60 m$^2$/g). Thus, the capacity of the beads to bind protein decreased with increasing porosity as the surface area decreases.

This experiment suggests that it is desirable to use beads with the lowest pore size capable of admitting the unconjugated protein.

EXAMPLE 11

This example demonstrates use of the invention with another and relatively low cost solid phase media. It also demonstrates the use of the method with another polysaccharide.

In this experiment, Neisseria PsA, a pH sensitive polysaccharide, was conjugated to TT, as follows.

In a first step, 25 mg of Neisseria PsA (obtained from SmithKline Beecham, Rixensart, Belguim) was solubilized at 10 mg/ml in water. At time zero,150 µl of CDAP at 100 mg/ml in acetonitrile was added. Thirty seconds, 150 µl of 0.2 M triethylamine (TEA) was added. At 1 minute, an additional 150 µl of TEA was added. At 2.5 minutes, 2 ml of hexanediamine (0.5 M in 0.1 M sodium borate, pH 9.3) was added. After 2 hours at room temp, the solution was dialyzed exhaustively into saline and assayed for amines and polysaccharide. The product (NH2-PsA) contained 6.7 amines per 100 kDa of Neiss PsA.

In the next step, Neiss PsA was conjugated to TT as follows. 220 µl of 0.75 M HEPES, 10 mM EDTA, pH 7.3 was added to 10 mg of NH2-PsA at 4.6 mg/ml in saline followed by 100 µl of 0.1 M N-hydroxysuccinimide iodoacetic acid (SIA, available from Pierce Chemical) in dimethylformamide (DMF). After a one hour reaction in the dark, the solution was concentrated using an Ulltrafree 30 device (Millipore) to about 1 ml and desalted on a P6DG column (1.5×15 cm, BioRad), equilibrated with saline. The desalted, iodoacetylated polysaccharide was concentrated to 870 µl using an Ultrafree 30 device.

100 µl of 0.15 M HEPES+2 mM EDTA, pH 7.3 was added to a solution of tetanus toxoid (7 mg at 14.5 mg/ml in saline) (obtained from SmithKline Beecham, Rixensart, Belguim), followed by 5 µl of 0.1 M N-hydroxysuccinimide S-acetylthioacetate (SATA, available from Pierce Chemical ) in DMF. After about 2 hours, the solution was desalted on a 1×15 cm P6DG column equilibrated with 10 mM MES+ 0.15 M NaCl, pH 6.5 and the concentrated to 0.49 ml using an Ultrafree 30 device.

The protein and polysaccharide solutions were combined and 150 µl of 0.75 M HEPES, 10 mM EDTA, 0.5 M hydroxylamine at pH 7.5 was added. After an overnight reaction at 4° C., the reaction was quenched by the addition of 30 µl of 10 mM mercaptoethanol and after an additional hour, 30 µl of 0.5 iodoacetamide was added.

0.75 ml of the solution was then dialyzed overnight into saline at 4° C. Following dialysis, the solution was brought to 2 ml with saline.

Silica with 150 angstrom pores (Davisil™ made by WR Grace Company, 200–425 mesh, grade 643, purchased from Aldrich (Catalog #23,681-0)) was suspended at 0.2 g/ml for 2 hours in deionized water. Thereafter, 500 µl of the conjugate solution (~4.4 mg/ml TT, 3.7 mg/ml PsA) was made pH 5 by the addition of 50 µl 1 M sodium acetate, pH 5, diluted by the addition of 350 µl saline and followed by the addition of 100 µl Davisil. At 35 and 65 min, 25 µl more of the Davisil was added. At 83 min, the Davisil was removed by centrifugation/filtration (Ultrafree MC, Millipore) and the Davisil rinsed with 2 100 µl aliquots of saline. The pools were then dialyzed into saline and assayed by SEC HPLC.

FIG. 9 shows the chromatograms before and after treatment. As indicated, the low molecular weight area was reduced from 59% of the total area to 21% of the total area by the treatment. Since there was poor resolution of the conjugated high molecular weight material, the data was also analyzed by comparing the peak heights of the high molecular weight material (at about 3 min) and the unconjugated protein (about 4 min). After accounting for dilutions and amounts injected on the column, it was determined that the high molecular weight material had a peak height of 70% of the high molecular weight material peak height of untreated conjugate. In contrast, the peak height of the low molecular weight material of the treated conjugate was only 12% of the starting low molecular weight peak height. Thus, recovery of the high molecular weight conjugate was very good, while the low molecular weight material was selectively removed.

EXAMPLE 12

This example demonstrates that the method successfully removes free protein from both concentrated and dilute solutions.

BSA was covalently linked to T2000 dextran using CDAP, as described above, and then dialyzed into saline. The solution contained 3.1 mg/ml BSA and 3.1 mg/ml dextran. 25 µl aliquots of the conjugate solution are diluted with saline, the pH adjusted by the addition of 1 M sodium acetate, pH 5 and 5 µl of Strataclean™ added. After 5 min on a rotator, the samples were filtered using a Millex Ultrafree MC device (Millipore)

Samples were diluted, if necessary and 50 µl injected onto the SEC HPLC column (Phenomenex Biosep SEC3000 150×78 mm, equilibrated with PBS). High MW (molecular weight) area representing conjugate and Low MW area representing free protein was determined

TABLE 8

| Concentration of BSA During Treatment | % Low MW* | Recovery of Conjugate** |
|---|---|---|
| 3.1 mg/ml (Untreated) | 32.8 | 100 |
| 2.2 mg/ml | 0 | 83.0 |
| 0.26 mg/ml | 6.1 | 90.7 |
| 0.078 mg/ml | 7.9 | 89.3 |

*low MW area divided by total area
**% of starting HMW area, adjusted for dilutions This data indicates that free protein is removed at both high and low total protein concentrations, with good recovery of the high MW material. Under the conditions used, the process was slightly less effective at removing free protein under dilute conditions but note that recovery of conjugate was higher. In all cases, there was a significant decrease in the free protein, thereby leading to the conclusion that the treatment is effective at for both concentrated and dilute solutions of conjugate and free protein. Unlike size exclusion chromatography, the process does not significantly dilute the conjugate further.

OTHER FEATURES OF THE INVENTION

This invention further relates to vaccines and immunogens that can be prepared from the conjugates produced in accordance with the invention. In a vaccine or immunogen, the conjugates produced according to the invention can be combined with a pharmaceutically acceptable carrier or delivery vehicle by conventional techniques known to those skilled in the art. Such products will contain an effective amount of the conjugate according to the invention, together with a suitable amount of vehicle, so as to provide the form for proper administration to a subject or other intended use. Vaccines may include alum or other adjuvants.

Exemplary pharmaceutically acceptable carriers or vehicles include, for example, sterile liquids, such as water and oils, including those of petroleum, animal, vegetable, or synthetic origin, such as peanut oil, soybean oil, mineral oil, sesame oil, and the like. Saline is a preferred vehicle when the pharmaceutical composition is administered intravenously. Aqueous dextrose and glycerol solutions also can be employed as liquid vehicles, particularly for injectable solutions. Suitable pharmaceutical vehicles are well known in the art, such as those described in E. W. Martin, *Remington's Pharmaceutical Sciences*, which source is entirely incorporated herein by reference.

The invention also relates to the method for treating a subject and inducing an immune response by administering an immunostimulatory amount of the vaccine according to the invention. The conjugates according to the invention may be administered to any subject for which the treatment may be beneficial, including mammals, especially humans, horses, cows, pigs, sheep, deer, dogs, and cats, as well as other animals, such as chickens. An "immunostimulatory amount" refers to that amount of vaccine that is able to stimulate the immune response of the subject for prevention, amelioration, diagnosis, or treatment of diseases or other conditions or ailments. The vaccines of the invention may be administered by any suitable route, but they preferably are administered by intravenous, intramuscular, intranasal, or subcutaneous injection.

In addition, the vaccines or immunogens in accordance with the invention can be used for any suitable purpose, such as for therapeutic, prophylactic, or diagnostic purposes.

In describing the invention, applicants have set forth certain theories in an effort to disclose how or why the invention works in the manner in which it works. These theories are set forth for informational purposes only. Applicants are not to be bound by any specific chemical or physical mechanisms or theories of operation.

Additionally, applicants have described several examples and processes for producing conjugates in accordance with the invention. While these procedures may be further optimized (e.g., optimizing the amount of solid phase material, contact times, etc.), such optimization of the process is a matter of routine experimentation.

While the invention has been described in terms of various preferred embodiments and specific examples, those skilled in the art will recognize that various changes and modifications can be made without departing from the spirit and scope of the invention, as defined in the appended claims.

We claim:

1. A method for removing protein from a liquid mixture containing free protein and at least one member selected from the group consisting of a protein-polysaccharide conjugate and a polysaccharide, the method comprising:
   contacting the liquid mixture with a solid phase, restricted-access media material, wherein the solid phase, restricted-access media material at least partially binds with the free protein and separates it from the liquid mixture, thereby providing a purified liquid containing a reduced amount of the free protein as compared to the amount of free protein present in the liquid mixture prior to contacting; and
   collecting the purified liquid.

2. A method according to claim 1, wherein the collecting includes separating the purified liquid from the solid phase, restricted-access media material.

3. A method according to claim 2, wherein the separating includes centrifuging.

4. A method according to claim 1, wherein the contacting includes agitating.

5. A method according to claim 1, wherein the contacting includes introducing the liquid mixture into a column including the solid phase, restricted-access media material.

6. A method according to claim 1, wherein the solid phase, restricted-access media material includes a plurality of silica particles.

7. A method according to claim 6, wherein the silica particles are porous such that at least a portion of the free protein enters pores in a silica particle, but the protein-polysaccharide conjugate or the polysaccharide has limited entry or no entry into the pores of the silica particles.

8. A process for producing a protein-polysaccharide conjugate, comprising:
   reacting a protein and a polysaccharide together under sufficient conditions to produce a liquid mixture containing a protein-polysaccharide conjugate and free protein;
   contacting the liquid mixture with a solid phase, restricted-access media material, wherein the solid phase, restricted-access media material at least partially binds with the free protein and separates it from the protein-polysaccharide conjugate; and
   collecting the protein-polysaccharide conjugate.

9. A method according to claim 8, wherein the collecting includes separating a liquid fraction including at least a portion of the protein-polysaccharide conjugate from the solid phase, restricted-access media material.

10. A method according to claim 9, wherein the separating includes centrifuging.

11. A method according to claim 8, wherein the contacting includes agitating.

12. A method according to claim 8, wherein the contacting includes introducing the liquid mixture into a column including the solid phase, restricted-access media material.

13. A method according to claim 8, wherein the solid phase, restricted-access media material includes a plurality of silica particles.

14. A method according to claim 13, wherein the silica particles are porous such that at least a portion of the free protein enters pores in a silica particle, but the protein-polysaccharide conjugate has limited entry or no entry into the pores of the silica particles.

* * * * *